United States Patent
Rümpler et al.

(10) Patent No.: US 8,231,938 B2
(45) Date of Patent: Jul. 31, 2012

(54) METHOD FOR PRODUCTION OF ENZYME GRANULES AND ENZYME GRANULES PRODUCED THUS

(75) Inventors: Karlheinz Rümpler, Weimar (DE); Michael Jacob, Weimar (DE); Mike Waskow, Weimar (DE)

(73) Assignee: Glatt Ingenieurtechnik GmbH, Weimar (DE)

( * ) Notice: Subject to any disclaimer, the term of this patent is extended or adjusted under 35 U.S.C. 154(b) by 1478 days.

(21) Appl. No.: 10/560,372

(22) PCT Filed: May 26, 2004

(86) PCT No.: PCT/EP2004/005662
§ 371 (c)(1),
(2), (4) Date: Dec. 12, 2005

(87) PCT Pub. No.: WO2004/108911
PCT Pub. Date: Dec. 16, 2004

(65) Prior Publication Data
US 2007/0093403 A1    Apr. 26, 2007

(30) Foreign Application Priority Data

| | | |
|---|---|---|
| Jun. 11, 2003 | (DE) | 103 26 231 |
| Dec. 9, 2003 | (DE) | 103 57 827 |
| Jan. 27, 2004 | (DE) | 10 2004 004 202 |
| Feb. 19, 2004 | (DE) | 10 2004 008 020 |

(51) Int. Cl.
    *B05D 7/00*    (2006.01)
(52) U.S. Cl. .................................................. 427/213
(58) Field of Classification Search .................. 427/213
See application file for complete search history.

(56) References Cited

U.S. PATENT DOCUMENTS

| | | | | |
|---|---|---|---|---|
| 3,443,621 | A | | 5/1969 | Dubreuil |
| 3,777,874 | A | * | 12/1973 | Birckhead ........................ 406/32 |
| 4,009,076 | A | * | 2/1977 | Green et al. .................. 435/187 |
| 4,100,263 | A | * | 7/1978 | Miller ............................ 423/383 |
| 4,233,007 | A | * | 11/1980 | Karlsson ............................. 425/7 |
| 4,354,450 | A | * | 10/1982 | Nagahama et al. ........... 118/303 |
| 4,736,895 | A | | 4/1988 | Huttlin |
| 4,858,552 | A | | 8/1989 | Glatt et al. |
| 4,876,198 | A | | 10/1989 | Markussen |
| 4,946,654 | A | | 8/1990 | Uhlemann et al. |

(Continued)

FOREIGN PATENT DOCUMENTS

CA      2 372 441      11/2001

(Continued)

*Primary Examiner* — Michael Cleveland
*Assistant Examiner* — Robert Vetere
(74) *Attorney, Agent, or Firm* — Volpe and Koenig, P.C.

(57) ABSTRACT

A method of producing enzyme granulates, enzyme granulates produced By the method, and the use thereof in formulations is provided, for example, for animal feed, foodstuffs, washing agents, rinsing agents or for pharmaceutical uses. The enzyme granulates have a high relative proportion of active enzyme, particular particle size, good shelf life, particularly small rounding factors and/or low residual moisture proportion, and further specific properties. The production of the enzyme granulates is achieved by linking of the thermal conditions in the injection zone and temperature conditions in the remainder of the apparatus. This is achieved by introduction of heated process gasses for drying exclusively in the injection zone. The secure introduction of articles into the injection zone is achieved by the specific geometric arrangement of the apparatus using gravity. The absolute value for enzyme activity of the enzyme granulates can be controlled by the addition of particles as seed material for the granules.

28 Claims, 1 Drawing Sheet

U.S. PATENT DOCUMENTS

| | | | |
|---|---|---|---|
| 4,968,443 A * | 11/1990 | Lambert et al. | 8/137 |
| 5,213,820 A | 5/1993 | Uhlemann et al. | |
| 5,575,086 A * | 11/1996 | Hartman et al. | 34/585 |
| 6,500,426 B1 | 12/2002 | Barendse et al. | |
| 6,579,365 B1 | 6/2003 | Jones et al. | |
| 6,740,632 B1 | 5/2004 | Jacob et al. | |
| 2003/0124224 A1 | 7/2003 | Barendse et al. | |
| 2003/0196598 A1 | 10/2003 | Jones et al. | |
| 2006/0105024 A1 * | 5/2006 | Andela et al. | 424/442 |

FOREIGN PATENT DOCUMENTS

| | | |
|---|---|---|
| DE | 25 55 917 | 11/1976 |
| DE | 101 46 778 | 4/2003 |
| EP | 0332929 A1 | 9/1989 |
| JP | 2002502254 A | 1/2002 |
| WO | 9855599 A2 | 12/1998 |
| WO | WO01/83727 * | 11/2001 |

* cited by examiner

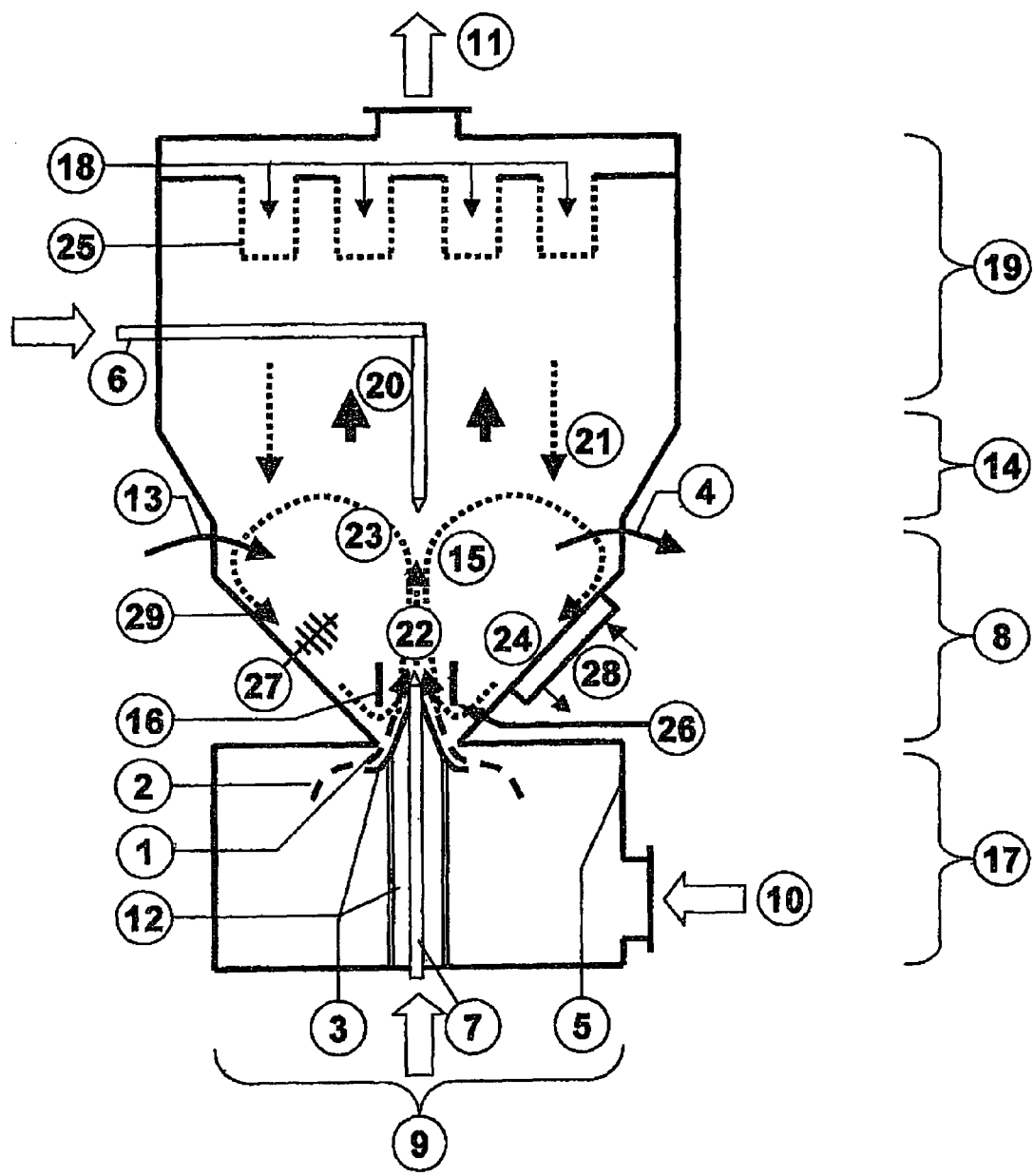

METHOD FOR PRODUCTION OF ENZYME GRANULES AND ENZYME GRANULES PRODUCED THUS

BACKGROUND

The invention relates to a method for producing enzyme granulates, enzyme granulates thus produced, and their use for producing formulations containing said enzyme granulates, (with their use simultaneously being part of a potentially preferred variant of the production method for the enzyme granulates), a method for producing enzyme granulates and/or the use of enzyme granulates thus produced, as well as further preferred embodiments of the invention shown in the following description and the subsequent claims.

Enzymes are used in a multitude of industrial fields in an ever increasing extent. This relates both to the amounts produced as well as the variety of forms of enzymes. Generally, enzymes are present in a liquid form or as a dry substance. Most recently, granulates have been used more and more as a preferred trade good by the users or by the processing industry. The granulates are characterized in advantageous features, such as easy dosing, very good flow characteristics, homogenous internal structures, high particle density, low dust content, as well as an even and well-closed surface. Due to the fact that enzymes can generally be characterized by their particular features, such as instability in an aqueous environment and their allergenic reactions, for example, the form of granulates has proven an advantageous trading form.

The stability of enzymes can be improved by converting them into a dry form. This can occur, for example, by spray drying, various agglomeration processes (wet granulation in mixers and/or fluidized bed devices (spray granulation).

Spray drying has the disadvantage that the devices require very large volumes and the powdery product contains a considerable content of dust.

In order to reduce this dust content, spray drying is frequently performed via a multi-stage drying device. It is disadvantageous that enzyme granulates produced in such multi-stage drying devices are provided with a poor, i.e. high rounding factor (lists the ratio of the surface of a granule in reference to the surface of a perfectly round granule) exceeding 1.6. Due to the low roundness and thus easily separating protruding sections, enzyme granulates with a rounding factor exceeding 1.6 quickly lead to a high dust content under mechanical stress occurring for example during packaging and transportation.

This dust content requires particular protective measures for the production personnel and the users as well as considerably higher expenses in plant engineering for the removal of dust, ventilation, and recycling of dust.

One potential method for producing enzyme granulates is presented in the buildup granulation in fluidized beds as published in WO 01/83727 A2. Here, a method is shown, in which the liquid enzyme formulation is injected via a nozzle into a fluidized bed. The dust developing in the process is separated from the exhaust and is recycled as seeds for the granulation process. The developing granulates are removed from the process using one or several gravity sifters arranged in the injection floor of the fluidized beds. The size of the granulates removed can be adjusted by controlling the gas amount in the sifter. Optionally, the granulates can additionally be coated. The process uses the fluidized bed process according to EP-A-0163836 and EP-A-0332929.

The described fluidized air process is characterized in an injection floor being provided over the entire cross-section of the fluidized bed for the homogenous distribution of the processing gas required for the fluidization and drying. The nozzles used for injecting the liquid spray vertically upwards and are directly integrated into the injection floor (EP-A-0332929) or surrounded by a sifter at the height of the injection floor (EP-A-0163836). The granulation seeds necessary for the process are produced by partial spray drying of the injected liquid by a partial non-covering (through spray) of the nozzles with the material in the fluidized bed. The mass of the fluidized bed is formed by a balance between the spray-dried seeds and by the recycled seed from sifting as well as the granulates discharged. A separation of granulates that are too large does not occur.

Caused by the introduction of the liquid, the particles contained in the fluidized bed are moistened in the injection area and drying of the moisture film on the surface of the particles occurs. Outside of the nozzles, in the remaining area of the fluidized bed essentially no drying of superficially moistened particles occurs. Instead, only a small portion of the moisture contained in the pores of the particles evaporates, which leads to an increase in the (core) particle temperature. However, in conventional fluidized beds an introduction of heated processing gas is necessary outside the spray area of the nozzles, as well, in order to mix the particles inside the device and to continuously move the particles in the injection zone. Due to the fact that the production of enzymes is temperature sensitive, these known processes cannot achieve an optimum yield in activity of enzymes (low relative activity in reference to the originally used enzyme activity, i.e., in addition to active enzymes, a large portion of deactivated or destroyed enzyme is present, which means that more enzyme must be used for the same amount of overall activity [absolute activity]). Additionally, uneven temperature distribution cannot be avoided in the production process.

In the process progression, the dwell time can be avoided in the systems described only in that the drying of the granulates does not occur up to the required final value and/or enzyme granulates of a smaller grain size are produced, which however influence the quality of the enzyme granulates. The enzyme granulates produced according to prior art have a high content of inactive carrier material and, thus a low absolute activity, a high content in deactivated enzyme (low relative activity), a low value of average grain size D50 (grain size, in which 50% by weight of the particles have a diameter smaller and 50% by weight of the particles a diameter greater than the average grain size D50), or a high moisture content, or usually two or three of these features.

For example, according to a method described in WO 01/83727 A2 a yield of enzyme activity higher than 85% can be achieved (in reference to the theoretically possible overall enzyme activity) having only small particles and/or a moisture content (residual moisture) of more than 5%.

On the other hand, WO 98/55599 describes a method for producing enzyme granulates using an extruder and a rounding device for use with a carrier material (such as corn starch). This method has also been described in example 2 of WO 01/83727.

Here, a yield of enzyme activity reaching 95% is achieved (relative enzyme activity) and a granulate having average grain sizes D50 of 600 μm, a moisture content of 5%, and a roundness factor of 1.4. This method is disadvantageous in that an enzyme preparation with 27% starch in the dry substance must be added to the mixture at a weight ratio of 1:2, in order to achieve a mixture that can be extruded. This way, the enzyme granulates yielded by this extrusion method is provided with a content of active enzyme material being less than 13% (absolute enzyme activity) in reference to the dry substance.

The enzyme granulates that can be yielded with the spray drying process according to WO 01/83727 results in granulates with a roundness factor in the preferred range from 1 through 1.6, though, and also with particles having an average grain size D50 of 620 μm (cf. table 2, experiment 2), however the content of inactive carrier material is much lower, resulting in the content of overall enzyme (active and deactivated) being higher than in the product of the process described in WO 98/55599. However, in the enzyme granulates according to WO 98/55599 it is disadvantageous that the relative portion of active enzyme, in reference to the overall amount of active and deactivated enzyme, is considerably lower, being 85%, than in the extrusion process, which is also discernible from example 2 mentioned in WO 01/83727.

According to the working mode described in WO 01/83727 the enzyme granulates are produced according to the method of to EP 0 332 929. This method is characterized in that the content of the bed adjusts itself (see EP 0 332 929, page 22, line 27). This way, the residence time cannot be controlled for a certain granulation performance. In example 1 the content of the fluidized bed amounts to 3 kg and the granulation yield is 1.5 kg/hour with the granulation occurring from an aqueous saline solution with a content of 23% by weight of dry matter. The residence time is also fixed to 2 hours in this case. Therefore, the residence time is here determined by the ratio of the content of the bed in reference to the granulation yield in kg/hour.

SUMMARY

The object of the invention is to provide a method for producing enzyme granulates, in particular with a low dust content, in which the enzyme granulates can be produced continuously or in separate charges largely avoiding uneven distribution of temperatures in the production process and in which the yield in (relative) activity of enzymes is increased. Simultaneously the ability to control the granulation during production is to be improved. In particular, an important object of the present invention is to provide a granulation method, which allows a shorter dwell time in reference to the fluidized bed methods known from prior art with otherwise identical conditions, such as composition of the enzyme concentrate, temperature of the drying air, average grain size D50 of the granulates, and roundness of the granulates. These objects are attained according to the invention in the characterizing features of claim 1, which additionally describe a particularly gentle process.

According to the invention, the production of enzyme-granulates occurs by tying the thermal conditions in the spray area to the temperature conditions in the remaining area of the device by way of the features mentioned in the characterizing part of claim 1. In particular, shorter material dwell times can be achieved in reference to the methods according to prior art, which results in a higher relative enzyme activity in the enzyme granulates produced by the method mentioned in claim 1. This is achieved in the method according to the invention in that the introduction of the heated processing gas for drying occurs primarily, i.e. particularly by more than 80%, preferably exclusively in the injection zone. The secure introduction of particles into the injection zone occurs particularly by the special geometrical design of the device using gravity; however, it can also occur pneumatically or by a combination of the geometrical design using gravity and pneumatic feeding.

The advantage of the solution according to the invention according to claim 1 is that the production conditions are adjusted to the features of the material to be produced. Uneven distribution of temperature is largely avoided, which also results in an increased yield of enzyme granulates.

The object of the present invention is also to provide enzyme granulates with a lower dust content and (relatively) higher content in active enzyme than in prior art combined with an average grain sized D50 ranging from 60 (in particular 100) μm up to 2000 μm, good shelf life, in particular a low roundness factor and/or a low moisture content.

The enzyme granulates produced according to the method of claim 1 according to the invention and in particular according to the dependent claim 16 are provided with these advantageous features. They can be used advantageously for the production of numerous types of interesting formulations, in particular such as the ones mentioned in claims 23 through 26, particularly by adding one or several suitable carrier materials and/or packaging in suitable applications.

Several advantageous embodiments are described in the dependent claims (which are included here by reference); they and their effect are further explained in the description.

The enzyme granulates produced according to the invention are highly concentrated and water soluble or water dispersible and have an average grain size D50 ranging from 60 to 2000 μm and are further characterized particularly in a dust content of <800, preferably less than 500 ppm according to the Haubach test at a ratio of active enzyme contents in reference to the sum of active and inactive enzyme contents (relative enzyme activity) amounting to 80% or more, in particular 88% or more. The crush strength of enzyme granulates produced is preferably at 10 MPa or higher, in a potentially preferred embodiment of the invention at 20 to 50 MPa, and the bulk density is at 500 g/l or more, in a potentially preferred embodiment at 550 to 850 g/l. The distribution of grain size is characterized in the ratio $d_{10}/d_{90}$ (definition: $d_{10}$ is the grain size, at which 10% of the mass of the granulates is smaller than this diameter, $d_{90}$ is the grain size, at which 90% of the mass of the granulate is smaller than this diameter), particularly at 0.4 or higher. The absolute phytase activity of enzyme granulates advantageously produced according to the invention (here, including phytase as the enzyme) is preferably equal or greater than 15000 FTU/g. Here, FTU is the enzyme activity, which releases 1 micro mol phosphate per minute at 37° C. under assay conditions (0.25 M sodium acetate, pH-value: 5.5; 51 nM sodium phytase).

BRIEF DESCRIPTION OF THE DRAWING

In the following the invention is explained in greater detail using a preferred embodiment. In the corresponding figures an arrangement for performing the method according to the invention is shown schematically.

DETAILED DESCRIPTION OF THE PREFERRED EMBODIMENT

The amount of heated processing gas 10 (generally heated air) necessary for drying the enzyme granulates to be produced is introduced into an inlet air chamber 17, having a rectangular cross-section 9 and limiting side walls 5. In the inlet air chamber 17, the processing gas 10 disperses and enters via the opening gaps 1 into the process chamber 8 in the form of gas jets 2. The processing stream preferably enters the gap 1 horizontally, is redirected preferably upwards by the deflection piece 3 into the processing chamber 8 and flows as a type of free stream into the device. Furthermore, the cross-section of the device can optionally be increased in the expansion zone 14 so that the speed of the processing stream continuously decreases upwards. The gas leaves the device in the form of exhaust 11 above the expansion zone 14 via the exhaust part 19, in which optionally a dust removal system (e.g. filter cartridges or textile filter elements) can be integrated.

In the processing chamber 8, an amount of particles are located, which can be entrained upward by the stream of processing gas. In the upper region of the processing chamber 8 as well as in the above-located expansion zone 14 the gas speed reduces so that the upward flowing particles fall laterally out of the gas stream 23 and back into the processing chamber 8. The processing chamber 8 is limited in the lower region by sloped lateral walls 29. The particles move by the effect of gravity and the lateral incline via the return zone 24 into the direction of the gas entry gap 1, where they are subsequently entrained once more by the processing gas into the processing chamber 8.

With this mechanism a very homogenous solid matter circulation 15 forms comprising an upward stream and a return in the direction of the processing gas entry. This also leads to a very high particle density in the core zone above the deflection part 3 even with very low amounts of particles in the processing chamber 8. In this area one or more nozzles 7 are arranged, spraying upwards directed to the stream of processing gas and serve to introduce the liquid enzyme formulation.

Through the high particle load in the core zone, very advantageous conditions result for the heat and material transfer in the injection zone 22. Furthermore, it is achieved that the liquid precipitates to the largest extent onto the particles and this way the surface of the particles is evenly moistened. The even moistening with a simultaneously high circulation of solid matter between the injection zone and the return zone 24 causes a very homogenous liquid film to form. The fluid evaporates by the drying process and leaves the device together with the exhaust 11. The solid matter contained in the formulation remains on the surface of the particles. This way, the granules grow very evenly and homogenously, which leads to a very narrow grain size distribution. A spray drying zone and subsequently a granulation zone is formed in the area of the nozzles 7 and 6 by the circular solid matter flow in the processing chamber 8.

The processing gas can remove a portion of the particles and fine matter and dust from the processing chamber 8 in the form of exhaust 20 loaded with solid matter. In order to precipitate these particles, the filter system, optionally integrated in the exhaust part 19, or the subsequent dust-removal arrangements can be used. In the case of an integrated dust removal device 25, for example, impulses of pressurized air 18 can be used in order to recycle the retained particles in the form of precipitated solid matter 21 into the processing chamber 8.

Compared to the fluidized beds with integrated filter devices, the dust recycling is facilitated such that the processing gas flowing directed upwards is essentially limited locally and thus the particles to be recycled can securely precipitate outside the gas stream. This mechanism is additionally enhanced by the suction effect in the proximity of the gas entry gap 1. Alternatively, particles precipitated from the exhaust or enzyme containing particles produced otherwise can be recycled into the processing chamber 8. For this purpose, different types of feeders 26 can be arranged in the lower section of the sloped side walls. Based on the high speed of the processing gas stream in the proximity of the gas entry gap 1, the fine particles are suctioned in and guided to the injection zone 22, where they are moistened with liquid and participate in the growth process.

Optionally integrated guide sheets 16 support the gas stream, increasing the suction effect and improving the feeding of the solid matter into the injection zone 22. Any potentially occurring agglomeration effects are minimized, because very high stream speeds occur in the injection zone and, thus, higher separation forces are present in the layers of the fluidized bed. Thus particles are separated and grow to almost spherical granules.

The flow profile of the processing gas in the processing chamber 8 also causes the fine particles recycled from the optionally integrated filter device into the processing chamber not to fall back into the injection zone 22. This way, the clogging of fine particles and subsequent processes of agglomerate formation are prevented.

For continuous processing, the device can optionally be provided with different input systems 13 for solid matter. This way for example, enzyme particles can be introduced into the process, which can be produced e.g. by milling of for example (too large) granulates and/or comprise granules that are too small, or which comprise one or several enzyme particles or enzyme containing educts in the form of otherwise produced, sufficiently fine dust and/or powder. Such enzyme particles or enzyme-containing educts (enzyme-containing intermediate products) can be products of other processing steps and methods (e.g., spray drying of enzyme solutions). The portion of said introduced enzyme-containing intermediate products amounts in particular to 1% by weight or more, in a potentially preferred embodiment of the invention to 5 to 20% by weight. Here, it is also possible and can be advantageous that the introduced enzyme particles are produced by a separate spray drying of an enzyme suspension. Here, in a potential advantageous embodiment it is also possible to introduce enzyme particles from the very beginning. These particles then serve as granulation seeds or as initial fillers for shortening the start-up time. Additionally, additives can be introduced into the process in a solid form here, which are to be embedded in the enzyme granulates. In another potentially preferred embodiment, instead of enzyme particles, other finely grained to coarse particulate material can be inserted as the seed material (preferred particle size smaller than 0.5 mm, preferably 0.1 to 0.2 mm), preferred inert (i.e. primarily enzymatically inactive) particulate material, for example for adjusting the enzymatic activity of the enzyme granulates, for example by introducing respective inert cores, such as inert salt grains, preferably before or particularly simultaneously to or subsequent to a step a. as above or later mentioned, at the beginning or during the granulation process. Here, the weight portion of the inert cores can amount, for example, from 0 to 95% by weight in the finished enzyme granulates.

Alternatively or in addition to this embodiment, during the drying and granulation process or during one or several parts of the these processes one or several inert materials can be added, such as particularly salts and/or bonding agents, not only as a core or seed material but also for diluting the enzyme or enzymes or particularly the (absolute, i.e. active and inactive enzyme components including) enzyme activity in the matrix of the enzyme granulates (i.e. distributed within parts or the entire matrix), which represents another particularly preferred embodiment of the invention. Here, the inert material can be added as a solid matter, for example by injection systems for solid matter such as 13, within the enzyme solution(s) [=liquid enzyme formulation(s)] (dissolved and/or in a suspension), and/or particularly in one or several (preferably aqueous) solutions separate from the enzyme solution, suspensions or melts, particularly in the gas streams 2, via feeders 26 and/or primarily via nozzles, for example in the injection zone 22. In the latter case, the solution or suspension or further melts of the inert material (e.g. a salt, such as an inorganic salt of a (for example alkaline) metal salt, such as sodium sulfate or sodium chloride, preferably in the presence of a bonding agent) and one or several separate nozzles or streams in addition to the nozzle or nozzles for injecting the enzyme solution, that are injected in particular in the area of the gas stream 2, or 3 or multi-material nozzles can be advantageously used. In this case, the liquids are injected into the respective nozzle sections separately and atomized, in a beneficial embodiment of the invention with additionally injected (preferably pressurized) gas, such as pressurized air. Advantageously, the nozzle is provided with a number of concentric pipes, via which the fluids and the air can be injected. For example, a first liquid can be injected via the interior pipe, a second liquid via a subsequent exterior coaxial circular gap, and the gas for injecting is provided via another coaxial circular gap positioned even farther outside (three way nozzle) or a first liquid is injected via the interior pipe, the gas for the injecting via an exterior coaxial circular gap, subsequent to the first one, a second liquid via another coaxial circular gap, positioned outside the latter, and more gas for injecting via a third coaxial circular gap, positioned on the exterior (four way nozzle).

This influx of inert material allows (as the seed in the core, as an addition in the matrix of the granulate or both), in high relative activity of the enzyme material used (low inactivation) to adjust very precisely any (i.e. between slightly above 0 through 100% of the maximum possible absolute activity), without changing the other parameters of the enzyme granulates such as the grain size or the freedom from dust. It can occur in a continuous operation or in a batch-operation. The content of the addition of inert material can be 0 to almost 100%, for example between 0.1 to 95% by weight in reference to the content of solid matter of the enzyme granulate. The grain size of the inert material can be arbitrary, when it is used diluted, the grain size for the use as a solid powder or as a suspension advantageously is at 200 μm or less, particularly at 100 μm or less.

Therefore, the invention also relates to the use of inert material in the above and later-described processes for adjusting a certain absolute enzyme activity of the enzyme granulates (enzyme activity per amount (of weight) of enzyme granulates.)

Furthermore, the device can be provided with discharge elements 4, in order to allow particles to be removed from the processing chamber 8. This can occur, for example, via a spillway or via a volumetric removal device (e.g. a rotary valve) or via a gravity sifter (e.g., a zigzag-sifter or a feed pipe sifter) impinged with a sifting gas.

Optionally, mechanical units 27 can be mounted in the processing chamber 8, preferably at the sloped walls in the area of the return zone 24, in order to create sufficient fine material as seeds for the granulate formation process. Furthermore, the return zone 24 can optionally be used for the positioning of heaters or other heat conducting units 28. For example, the device wall can be embodied as a double wall, in order to use it, for example, for heating or cooling by using liquid or gaseous heat conductors. Alternatively, microwave heaters can also be used in order to afterdry or preheat the particles in the return zone 24.

In the processing chamber 8 or in the above-positioned parts of the device, e.g., the expansion zone 14 and the exhaust part 19, optionally spray nozzles 6 can be arranged, preferably spraying downwards, but also sometimes upwards. Here, the liquid enzyme formulation can also be injected in, for example, in order to create granulation seeds in the device by spray drying. Alternatively, additives or other components can be injected by some of the spray devices 6 and 7 in a liquid form and, thus be homogenously be embedded in the granule structure. When the nozzles 7 pass the feeding air chamber 17, impinged by hot air, the parts guiding liquids can optionally be provided with insulations or different cooling systems 12, in order to prevent damage to the liquid formulations.

In order to reduce the water sensitivity and/or to control the water solubility of the enzyme granulates produced according to the invention they can be provided with a protective layer by way of coating in a subsequent, separate process.

As another advantage of the process according to the invention the very simple design has to be mentioned, which combines a high operational security with resistance to malfunctions and a very good provision for cleaning. This way, improved production conditions are provided, particularly with regard to the hygienic requirements when changing products for biological materials.

EXAMPLES

In the following, the invention is explained in concrete exemplary embodiments without restrictions.

Example 1

Production of Enzyme Granulates

An enzyme formulation, which contained a stabilizer and binder components in addition to the enzyme solution and a final concentration of solid matter amounting to approximately 22 percent in mass, was injected by nozzles into a device, which is characterized in the above-described construction. The processing chamber has a rectangular cross-section and has a cross-sectional surface of $0.15 \times 0.2 = 0.03$ m$^2$ above the sloped side walls and a height of approximately 1 m. The influx of the processing air flow heated to approximately 140° C., amounting to approximately 180 kg/h occurs via 2 gas feeding gaps extending lengthwise through the device. The liquid formulation was injected via a two-material nozzle, spraying upward and being vertically impinged by pressurized air, into the processing air stream with a mass flow amounting to approximately 50 g/min. Approximately 500 g enzyme particles are provided in the processing chamber. The processing air cools by the evaporation process and leaves the device with approximately 45° C. The dedusting of the exhaust air occurs by a cyclone separator positioned subsequent to the device, and the separated solid matter is gravimetrically fed as seed material into the processing chamber in the proximity of the gap. The removal of the granulates from the processing chamber occurs at the face, using a sieve. The content of fine matter separated at the sifter is recycled pneumatically into the processing chamber. The granulates removed have a non-compressed bulk density of 800 g/l and the following distribution of grain size (sieve analysis):

| | |
|---|---|
| >400 μm: | 0.8% by mass |
| 315 ... 400 μm: | 6.8% by mass |
| 250 ... 315 μm: | 15.3% by mass |
| 160 ... 250 μm: | 42.3% by mass |
| 100 ... 160 μm: | 24.9% by mass |
| 0 ... 100 μm: | 9.9% by mass |

Example 2

Enzyme granulates with phytase from *Aspergillus Niger*

Commercially available phytase (natuphos 5000L, BASF, Ludwigshafen, Germany) is filtered with de-mineralized water and an ultrafine filter with a pore size preventing the passing of the enzyme, in order to remove preservatives and salts. The enzyme is subsequently filtered ultrafinely, in order to yield a highly concentrated liquid enzyme preparation.

Polyvinyl alcohol as a binder is added to 25% by weight of said liquid enzyme preparation with a phytase activity of 24 000 FTU/g and a dry content of 25% by weight. The remaining 75% by weight of the solution is spray dried at an air entry temperature of 180° C. and an exhaust temperature of 70° C. in the device mentioned in example 1.

The spray-dried enzyme power is collected in a container connected in a dust-tight manner. An enzyme powder is yielded with a phytase activity of 90 000 FTU/g and 95% dry substance. The container with the spray-dried enzyme powder is mounted to the insertion system 13 via a dust-tight coupling. The liquid enzyme preparation is sprayed with a dosing pump through a nozzle into the processing chamber 8.

Liquid enzyme preparation and enzyme powder is added in a mass ratio of 4:1. The entry temperature amounts to 120° C., the exhaust temperature to 60° C. A phytase granulate develops having the features shown in table 1. The content of active and inactive phytase is determined by the process for characterizing *aspergillus ficuum* phytase described in EP 0 420 356, which is incorporated herein by reference.

TABLE 1 features of phytase granulate according to example 2

| Feature | Numerical values |
| --- | --- |
| Roundness factor | 1.4 |
| Residual moisture | 5% |
| Yield of activity | 97% |
| Content in active enzyme/ total enzyme content | 95% |
| Activity | 83 000 FTU/g |
| Average grain size D50 | 640 μm |
| Grain size ration $d_{10}/d_{90}$ | 0.7 |
| Bulk density | 590 g/l |

Example 3

Utilization of Salt/Binder Solutions

A pilot plant with 4 inlet air chambers and 4 nozzles was used. Protease was used as the enzyme. Inorganic alkaline metal salts and common binders were used for the salt/binder components. The content of the components is listed in % by weight ("%").

Pure enzyme solution and salt binder solution were each injected separately via nozzles, with the diluted amount of water per nozzle being adjusted as evenly as possible:

|  |  | Enzyme solution (cold) | Salt-binder-suspension (65° C.) |
| --- | --- | --- | --- |
| Chambers |  | 3 | 1 |
| Concentration | % | 18 | 50 |
| Spray amount | kg/h | 22 | 12 |
| Water per nozzle | kg/h | 6.0 | 6 |
| Portion in the Product |  | 39.8 | 60.2 |
| Inlet air temperature | ° C. | 125 |  |
| Exhaust air temperature | ° C. | 55 |  | b) enzyme solution and salt-binder solution was added via all nozzles into a mixture:

|  |  | Enzyme content | Salt-binder-content |
| --- | --- | --- | --- |
| Chambers |  | 4 |  |
| Portion in the solution | % | 10 | 24 |
| Spray amount | kg/h | 30 |  |
| Water per nozzle | kg/h |  | 4.95 |
| Portion in the product | % | 29.4 | 70.6 |
| Inlet air temperature | ° C. | 115 |  |
| Exhaust air temperature | ° C. | 50 |  | c) enzyme solution and salt-binder solution was injected separately via three-material-nozzles

|  |  | Enzyme solution (cold) | Salt-binder-suspension (65° C.) |
| --- | --- | --- | --- |
| Chambers |  | 4 |  |
| Concentration | % | 15 | 50 |
| Spray amount | kg/h | 15 | 20 |
| Water per nozzle | kg/h |  | 5.7 |
| Portion in the product | % | 18.4 | 81.6 |
| Inlet air temperature | ° C. | 120 |  |
| Exhaust air temperature | ° C. | 55 |  | d) the enzyme-binder solution was sprayed and salt powder was added in a solid form

|  |  | Enzyme-binder-solution (cold) | Salt-powder <30 μm |
| --- | --- | --- | --- |
| Chambers |  | 4 |  |
| Portion in the solution | % | 15 | 100 |
| Spray amount | kg/h | 20 | 25 |
| Water per nozzle | kg/h |  | 4.3 |
| Portion in the product | % | 10.7 | 89.3 |

In summary, the following can be stated:

The invention relates to a method for producing enzyme granulates. The object of the invention is to provide a method for producing enzyme granulates, in which the enzyme granulates can be produced continuously or by charge, largely avoiding uneven distribution of temperature during the production process and increasing the yield in activity in the enzymes. Simultaneously the ability to control the granulation is to be improved during the production. The enzyme granulates produced with this method and their use are disclosed.

According to the invention, the production of enzyme granulates occurs by a connection of the thermal conditions in the spray area and the temperature conditions in the remaining areas of the device. This is achieved in the method according to the invention in that the feeding of heated processing gas for drying occurs exclusively in the injection zone. The safe introduction of particles into the injection zone occurs by the special geometrical design of the device using gravity.

The invention claimed is:

1. A method for producing enzyme granulates, comprising:

a. injecting at least one liquid enzyme formulation via nozzles into a heated solids-laden processing gas stream, the processing gas stream entering a device, via at least one opening gap (1) which is rotationally symmetrical or elongated that leads into a process chamber (8) in the form of gas jets and the processing stream entering the at least one gap (1) horizontally and being redirected upwards by a deflection part (3) into the processing chamber (8) and flowing as a type of free stream into the device, b. subjecting moistened solids in the heated gas stream to a drying and granulation process, c. separating the particles from the gas stream after a residence time, and returning the particles into a processing chamber, where in an upper region of the processing chamber (8) and in an expansion zone (14) located above the process chamber (8), gas speed reduces so that upward flowing particles fall laterally out of the gas stream (23) and fall back into the processing chamber (8), which is limited in a lower region by sloped lateral walls (29) defining a lateral incline, and by the effect of gravity and the lateral incline via a return zone (24) move towards the as least one of the gas entry gap (1), d. directing, as a result, the particles into the gas entry area where they are subsequently entrained once more by the processing gas into the processing chamber (8), e. separating fine particles, dust, and particles from the particles entrained by the processing gas and returning the fine particles, dust, and particles to the process as seed material for granulate formation, f. forming a circular flow of solid matter, through material return into the gas stream, arranged in an axial direction of the reaction chamber, g. adding at least one inert material as an addition into the enzyme granulate matrix or parts therefrom for diluting the enzyme, wherein the at least one inert material is added in at least one of: solutions, suspensions or melts, which is separate from the enzyme formulation, and h. atomizing the at least one inert material via at least one inert material atomizing three way nozzle or four way nozzle that is separate from at least one liquid enzyme atomizing nozzle for atomizing the liquid enzyme formulation during the drying and granulation process, with both types of nozzles being present in an injection zone (22) in the core zone above the deflecting part (3);

wherein the average value of the residence time of the enzymes in the processing chamber amounts to less than 1.5 hours.

2. A method according to claim 1 wherein the enzyme granulates are removed from the processing chamber by a sifting device.

3. A method according to claim 1 wherein the enzyme granulates are removed from the processing chamber via volumetric removal units.

4. A method according to claim 1 wherein the enzyme granulates removed from the process that are too small or too big are separated from the finished goods.

5. A method according to claim 4, wherein the enzyme granulates removed from the process that are too small are returned into the processing chamber as seed material.

6. A method according to claim 5, wherein the enzyme granulates returned to the processing chamber are thermally retreated.

7. A method according to claim 6, wherein the enzyme granulates returned into the processing chamber are dried or preheated.

8. A method according to claim 6, wherein the enzyme granulates returned into the processing chamber are milled.

9. A method according to claim 4, wherein the enzyme granulates removed from the process that are too large are milled by a milling device and returned into the processing chamber as seed material.

10. A method according to claim 1, wherein the enzyme granulates are made from various additives and in various mixing ratios.

11. A method according to claim 1, wherein, the material particles are subjected to a granulation process after prior spray drying.

12. A method according to claim 1, wherein 1% by weight or more, of a powdery ready-made granulation product, produced according to the method and/or otherwise produced enzyme particles and/or one or more enzyme containing intermediate products, selected from enzyme containing powder or dust, is added to the granulation process.

13. A method according to claim 1, wherein the enzyme granulates produced are coated in a subsequent step by coating with a water-protecting layer.

14. A method according to claim 1, wherein before or simultaneously to or after step a., or during the granulation process, fine-grained to coarse particular material is added as the seed material for the drying and granulation process.

15. A method according to claim 1, wherein the enzyme granulates produced, have a roundness factor of 1 to 1.6, an average grain size D50 of 60 to 2000 μm, (i), wherein when a content of the active enzyme in reference to a sum of active and inactive enzyme content amounts to more than 85% up to 88%, the average grain size D50 lies in the range from 650 to 2000 μm, (ii) wherein when a portion of the active enzyme, as defined above, is more than 88% up to 91%, the average grain size D50 is in the range from including 470 to less than 650 μm, (iii) wherein when the portion of the active enzyme, as defined above, is more than 91% up to 95%, the average grain size D50 is at 230, including to less than 470 μm, and (iv) wherein when the portion of the active enzyme, as defined above, amounts to more than 95%, the average grain size D50 ranges from 60 to less than 230 μm, and a residual moisture is below 5% by weight.

16. A method according to claim 15, wherein a weight ratio of inactive material including inactive enzyme in reference to active enzymes amounts to less than 7:1 in reference to a dry weight.

17. A method according to claim 16, wherein the enzyme granulate has an average grain size of 60 through 800 μm, wherein a dust content according to the Heubach test is less than 800 ppm.

18. A method according to claim 17, wherein a pressure resistance of the enzyme granulates is equal or more than 10 MPa.

19. A method according to claim 18, wherein a grain size distribution of the enzyme granulates, defined by a ratio of d10/d90, is equal or greater than 0.4.

20. A method according to claim 18, wherein a bulk density of the enzyme granulate is equal or greater than 500 g/l.

21. A method according to claim 15, comprising phytase as an enzyme, the phytase activity of the enzyme granulates is equal or greater than 15 000 FTU/mg.

22. A method according to claim 15, further comprising using the enzyme granulates as an addition or a sole effective component in the production of formulations for food, cleaning, or pharmaceutical purposes.

23. The method according to claim 22, wherein the enzyme granulate is used for the production of feed.

24. The method according to claim 22, wherein the enzyme granulate is used for the production of food.

25. The method according to claim 22, wherein the enzyme granulate is used for the production of a laundry or dishwashing detergent.

26. The method according to claim 22, further comprising using the enzyme granulates as addition or sole effective agent in the production of formulations for food, cleaning, or pharmaceutical purposes.

27. The method according to claim 26, further comprising using the enzyme granulate for the production of feed, food or a laundry or dishwashing detergent.

28. A method according to claim 1, wherein one or more material nozzles and a gas for atomizing one or more solutions or suspensions of one or more inert materials are used.

* * * * *